US00PP24013P3

(12) United States Plant Patent
Cesarini

(10) Patent No.: US PP24,013 P3
(45) Date of Patent: Nov. 5, 2013

(54) ***THUJA* PLANT NAMED 'CONCESARINI'**

(50) Latin Name: ***Thuja occidentalis / THUJA* Plant**
Varietal Denomination: Concesarini

(75) Inventor: Gabriel Cesarini, Denton, MD (US)

(73) Assignee: CP Delaware, Inc., Wilmington, DE (US)

( * ) Notice: Subject to any disclaimer, the term of this patent is extended or adjusted under 35 U.S.C. 154(b) by 97 days.

(21) Appl. No.: 13/373,190

(22) Filed: Nov. 8, 2011

(65) Prior Publication Data

US 2013/0117897 P1 May 9, 2013

(51) Int. Cl.
*A01H 5/00* (2006.01)

(52) U.S. Cl.
USPC ..... Plt./213

(58) Field of Classification Search
USPC ..... Plt./213
See application file for complete search history.

*Primary Examiner* — Kent L Bell
(74) *Attorney, Agent, or Firm* — Buchana Ingersoll & Rooney PC

(57) ABSTRACT

A new *Thurja occidentalis* (i.e., American Arborvitae) plant is provided which originated as a whole plant mutation of the 'Linesville' variety (non-patented in the United States). Unlike the parental variety, the new plant displays a distinctive much lower growing dense globular rounded growth habit. Good winter hardiness is displayed and the plant resists sun and winter burning. The plant is well suited for providing attractive and uniform ornamentation close to ground level.

1 Drawing Sheet

Botanical/commercial classification: *Thuja occidentalis/ THUJA* Plant.

Varietal denomination: cv. Concesarini.

SUMMARY OF THE INVENTION

Many varieties of *Thuja occidentalis* plants (i.e., American Arborvitae plants) are known in the horticultural industry. Among these is the 'Linesville' variety (non-patented in the United States) which is known to display a tight and compact growth habit with a dwarf mounded globe and soft sage-green juvenile foliage.

The new variety was discovered as a whole plant mutation of unknown causation among plants of the 'Linesville' variety growing at the nursery of the originator at Denton, Md., U.S.A. The new variety was observed to display a growth habit that was considerably lower than even its 'Linesville' parent. Had the new variety not been discovered and preserved it would have been lost to mankind.

It was found that the new *Thuja* plant of the present invention possesses the following combination of characteristics:

(a) displays a much lower growing dense globular rounded growth habit than the 'Linesville' variety (non-patented in the United States),
(b) displays good winter hardiness,
(c) resists sun and winter burning, and
(d) is well suited for growing as attractive uniform ornamentation close to ground level.

No cones have been observed during observations of the new variety to date.

The new variety of the present invention can be readily distinguished from its 'Linesville' variety parent and all other *Thuja* varieties known to the discoverer.

As indicated, the growth habit of the new variety is considerably lower than that of the 'Linesville' variety. When compared to the 'Bogozam' variety (U.S. Plant Pat. No. 8,215), the new variety forms greyed-green foliage unlike the golden foliage coloration of the 'Bogozam' variety.

The new variety is well suited for providing attractive uniform low-growing ornamentation in gardens and in the landscape over an extended period of time.

Asexual reproduction of the new variety at West Grove, Pa., U.S.A., beginning in 2006, by the use of semi-hardwood cuttings has demonstrated that the distinctive characteristics of the new variety of the present invention are reliably transmitted from one generation to another. Accordingly, the new variety reproduces in a true-to-type manner by such technique.

The new variety has been named 'Concesarini' and will be marketed under the PANCAKE trademark.

BRIEF DESCRIPTION OF THE PHOTOGRAPH

The accompanying photograph shows as true as it is reasonably possible to make the same in color illustrations of this character a typical specimen of the new variety of the present invention.

Such plant of the present invention is shown at the right of the photograph.

For comparative purposes, a plant of the 'Lineville' variety is shown at the left of the photograph.

The depicted plants were approximately three years of age and were growing outdoors in the ground under full sun at West Grove, Pa., U.S.A. The significantly lower growth habit of the new variety is readily apparent.

DETAILED DESCRIPTION

The following description is based upon the observation of typical plants of the new variety at an age of approximately three years during the month of October while growing in containers in full sun at West Grove, Pa., U.S.A. The growing conditions approximated those employed for the commercial production of *Thuja* plants. The chart used in the identification of colors is The R.H.S. Colour Chart of The Royal Horticultural Society, London, England, 1995. Common color terms are to be accorded their customary dictionary significance.

Plant:

*Height.*—Approximately one foot for a three-year-old plant.

*Width.*—Approximately 2½ feet for a three-year-old plant.

*Growth habit.*—Extremely low growing, compact, dense, globular, rounded, perennial evergreen shrub.

*Growth rate.*—Moderate.

*Propagation.*—Is well asexually reproduced through the use of semi-hardwood cuttings.

*Roots.*—Fibrous.

Stems:

*Shape.*—Generally oval.

*Diameter.*—Commonly approximately 1 cm for main branches, and approximately 0.3 cm for lateral branches.

*Length.*—Commonly approximately 3 cm for main branches, and approximately 17 cm for lateral branches.

*Texture.*—Glabrous and knobby with scales.

*Color.*—New growth in sprays commonly is Grey-Brown Group 199C with scales of near Greyed-Orange Group 167D, young branches commonly are Greyed-Orange Group 166B with scales of near Greyed-Orange Group 166A, and mature branches commonly are near Greyed-Orange Group 177A.

*Internode length.*—Commonly approximately 3 cm on average at the base and approximately 2 cm on average approaching the tip.

Branching:

*Arrangement.*—Alternate, main stem arises from a base with numerous secondary branches.

*Frequency.*—Commonly approximately 34 lateral branches on average per main stem.

*Aspect.*—Main stems are substantially upright, lateral stems are held at an angle of approximately 45° from a main stem, and substantially flat sprays extend outwards.

Foliage:

*Arrangement.*—Numerous leaves on planar branchlets, closely alternate or opposite, and scale-like decussate.

*Form.*—Simple, facial pair keeled, flat pair flattened and oblong.

*Leaf size.*—Approximately 2 mm in length on average, and approximately 1 mm in width on average.

*Leaf quantity.*—Commonly approximately 15 leaves per cm on lateral branchlets.

*Apex.*—Apiculate.

*Base.*—Cuneate.

*Venation.*—Not apparent.

*Margin.*—Entire.

*Texture.*—On upper and lower surfaces glabrous, smooth, and glossy.

*Color.*—New growth commonly is near Greyed-Green Group 191A on the upper and lower surfaces, and mature growth commonly is a blend of near Green Group 137A and near Green Group 141A on the upper and lower surfaces.

*Fragrance.*—Somewhat acrid when crushed.

Development:

*Resistance to disease.*—No disease susceptibility has been encountered during observations to date.

*Resistance to pests.*—No pest susceptibility has been encountered during observations to date.

*Weather tolerance.*—Has been observed to be tolerant to drought, rain and wind, and temperatures ranging from 0° to 100° F.

*Cold hardiness.*—U.S.D.A. Hardiness Zone Nos. 3 to 7.

The new 'Concesarini' variety has not been observed to date under all possible environmental conditions. Accordingly, it is possible that the phenotype may vary somewhat with variations in the environment, such as temperature, light intensity, day length, and other cultural conditions without variance of the genotype.

I claim:

1. A new and distinct *Thuja* plant having the following combination of characteristics:

(a) displays a much lower growing dense globular rounded growth habit than the 'Linesville' variety (non-patented in the United States), (b) displays good winter hardiness, (c) resists sun and winter burning, and (d) is well suited for growing as attractive uniform ornamentation close to ground level;

substantially as illustrated and described.

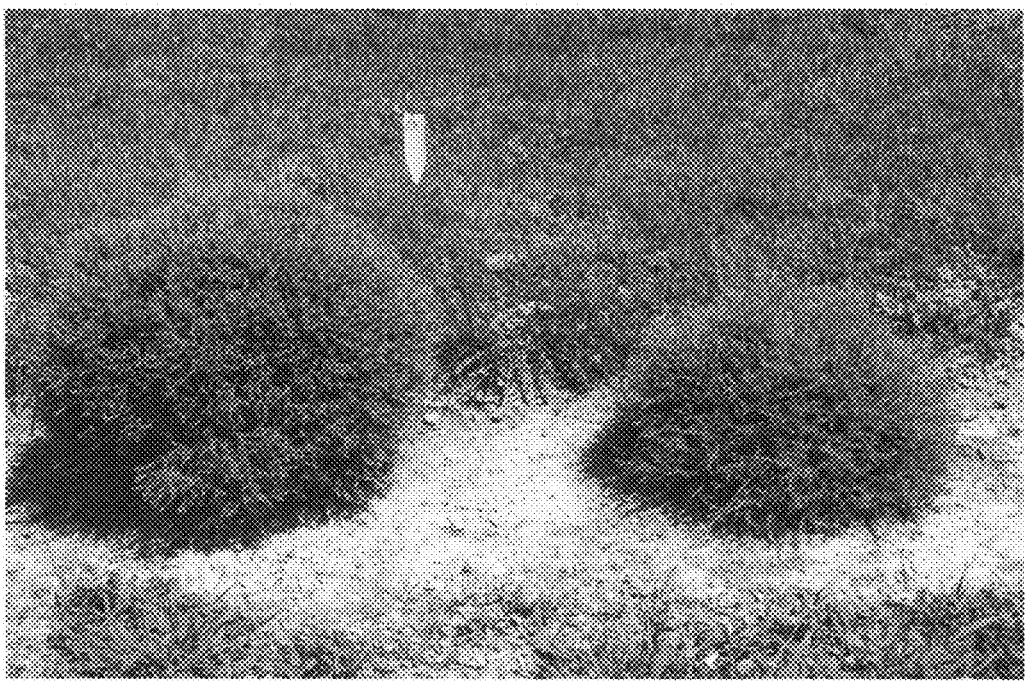

* * * * *